United States Patent
Amato

(12) 
(10) Patent No.: US 6,240,839 B1
(45) Date of Patent: Jun. 5, 2001

(54) DEVICE FOR PROOFING DOUGH

(76) Inventor: Giacomo Amato, Tudor Ct., Apt. K8, East Hampton, NJ (US) 08060

( * ) Notice: Subject to any disclaimer, the term of this patent is extended or adjusted under 35 U.S.C. 154(b) by 0 days.

(21) Appl. No.: 09/451,005

(22) Filed: Nov. 29, 1999

(51) Int. Cl.⁷ ............................................. A21C 13/00
(52) U.S. Cl. .......................... 99/468; 99/486; 99/493; 73/169
(58) Field of Search .................. 99/486, 493, 468, 99/341–344; 426/19, 27, 231, 496, 418; 73/169, 319

(56) References Cited

U.S. PATENT DOCUMENTS

| | | | |
|---|---|---|---|
| 1,429,269 | * 9/1922 | Banks . | |
| 1,654,897 | * 1/1928 | Rosenblum . | |
| 3,518,949 | 7/1970 | Stock | 107/7 |
| 4,483,243 | 11/1984 | Cote | 99/468 |
| 4,667,591 | * 5/1987 | Garbar et al. | 99/483 |
| 5,072,666 | 12/1991 | Hullstrung | 99/468 |
| 5,766,373 | * 6/1998 | Mraz | 426/231 |
| 5,871,792 | * 2/1999 | Weiss et al. | 426/233 |

* cited by examiner

Primary Examiner—Keith Hendricks
Assistant Examiner—Drew Becker
(74) Attorney, Agent, or Firm—LaMorte & Associates

(57) ABSTRACT

A device and method for storing dough as the dough rises, wherein an indication is provided when the dough has risen to the proper volume. A batch of leavened dough is placed in a container. A lid is provided for covering the leavened dough in the container. The lid defines an aperture that extends through said lid. An alarm assembly is provided that is capable of providing a visual and/or an audible alarm when triggered. The alarm assembly is positionable on the lid, wherein the lid supports the alarm assembly over the leavened dough. A contact element is provided that rests upon the leavened dough within the container. The contact element rises with the dough and contacts the alarm assembly through the aperture in the lid when the leavened dough rises to a predetermined volume. When the contact element reaches the alarm assembly, the contact element triggers the alarm assembly. A person seeing and/or hearing the alarm therefore knows that the dough has risen to the proper amount.

9 Claims, 2 Drawing Sheets

DEVICE FOR PROOFING DOUGH

BACKGROUND OF THE INVENTION

1. Field of the Invention

In general, the present invention relates to storage devices for retaining dough as the dough rises. More particularly, the present invention relates to devices that retain dough and provide a visual indication as to when the dough has risen to a predetermined volume.

2. Description of the Prior Art

There are many different food items that are made from dough. As a result, there are many different types of dough recipes. However, most all dough recipes contain the common ingredients of flour, water and yeast. When yeast is added to a dough recipe, the dough begins to rise. If the dough is not allowed to rise for the proper amount of time, the dough may not bake properly and the resultant food may not be as palatable as desired. Similarly, if the dough is allowed to rise for too long, then the dough may become sticky and loose its elasticity. Again food products made from such dough may be unusable by a baker or not as palatable as desired.

Letting dough rise for the proper amount of time is an art learned by bakers. However, the time it takes dough to rise is dependent upon many variables such as temperature, humidity, dough ingredients and the strain of yeast used in the dough. Accordingly, even the most skilled of bakers may sometimes misjudge the rise time of dough and use the dough either prematurely or after it has peaked.

To help take the guess work out of proofing dough, many devices have been invented that enable the dough to rise in a controlled environment. In this manner, the dough is more likely to rise in the same period of time, batch after batch. Such prior art devices are exemplified by U.S. Pat. No. 5,076,666 to Hullstrung, entitled Dough Proofing Chamber; U.S. Pat. No. 4,483,242 to Cote, entitled Apparatus For Rising Dough; and U.S. Pat. No. 3,518,949 to Stock, entitled Apparatus For Conditioning Dough And Baked Goods.

The prior art devices listed above provide environmentally controlled chambers in which dough is placed. Such prior art devices tend to be large and expensive, thereby making such devices impractical for many bakers. A good example of a place where such prior art proofing chambers are impractical is a pizzeria. In a pizzeria, the majority of the kitchen space is consumed by the large ovens used to cook the pizzas. As such, there is little room for a large dough proofing chamber for the pizza dough. Furthermore, in a pizzeria, dough is constantly being made and used throughout the day. Accordingly, it is not practical to proof large batches of dough at the same time in a proofing chamber. Rather, to ensure freshness, small batches of dough need to made at different times during the day.

A need therefore exists for a device and method that can be used to proof small batches of dough in a space efficient and cost efficient manner. A need also exists for a dough proofing device that provides a person with a visual indication as to when a specific batch of dough has risen for the proper period of time. These needs are met by the present invention as described and claimed below.

SUMMARY OF THE INVENTION

The present invention is a device and method for storing dough as the dough rises, wherein an indication is provided when the dough has risen to the proper volume. A batch of leavened dough is placed in a container. A lid is provided for covering the leavened dough in the container. The lid defines an aperture that extends through said lid. An alarm assembly is provided that is capable of providing a visual and/or an audible alarm when triggered. The alarm assembly is positionable on the lid, wherein the lid supports the alarm assembly over the leavened dough.

A contact element is provided that rests upon the leavened dough within the container. The contact element rises with the dough and contacts the alarm assembly through the aperture in the lid when the leavened dough rises to a predetermined volume. When the contact element reaches the alarm assembly, the contact element triggers the alarm assembly. A person seeing and/or hearing the alarm therefore knows the dough has risen to the proper volume.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

Although the present invention device and method can be used to store many types of leavened dough, such as bread dough and the like, the present invention device and method are particularly well suited for use in storing pizza dough. Accordingly, the illustrated examples of the present invention device will show applications where the device is being used to hold pizza dough as it rises, in order to set forth the best mode contemplated for the present invention.

Figure 1:
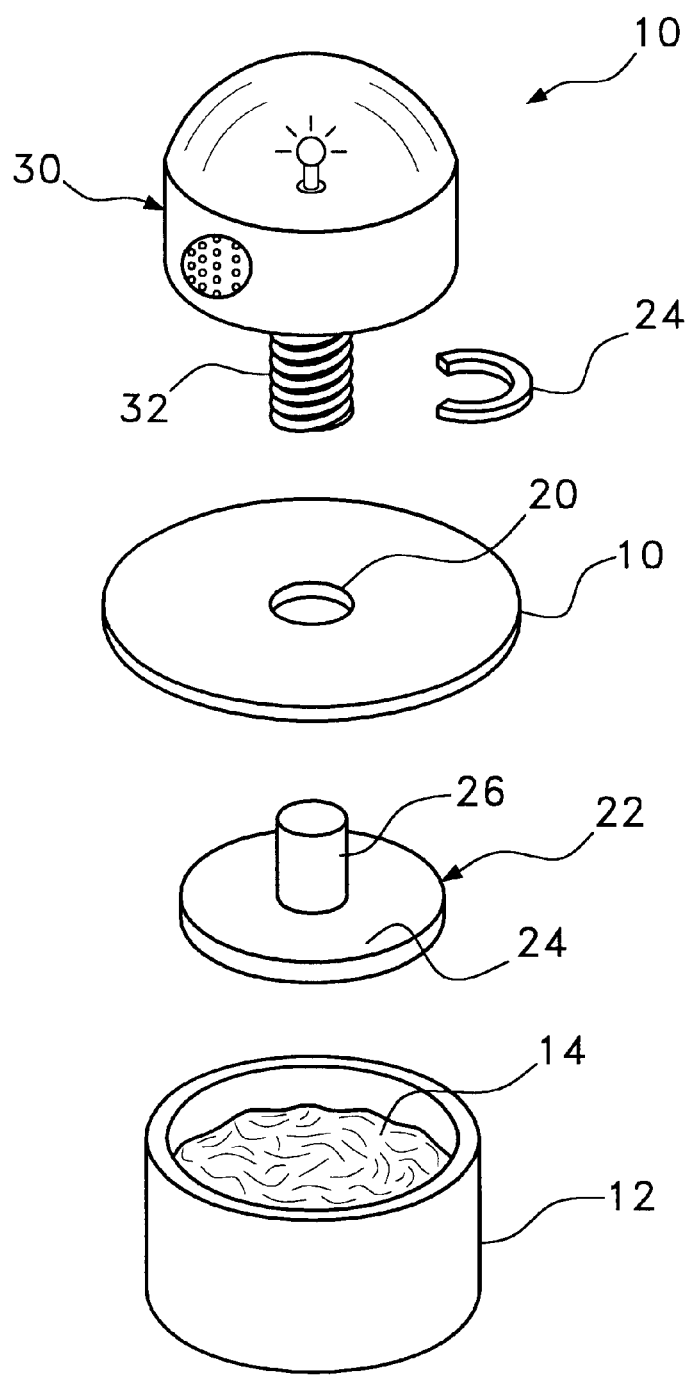
FIG. 1 is an exploded perspective view of an exemplary embodiment of the present invention device, shown in conjunction with a container filled with pizza dough.

Referring to FIG. 1, a first embodiment of the present invention device 10 is shown in conjunction with a traditional pizza dough container 12. In a pizzeria, pizzas are made in different sizes. Accordingly, batches of dough are also made in different sizes. The dough for a large sicilian pizza requires a larger container than does the dough for a small regular pizza. Accordingly, it should be understood that the container 12 shown in FIG. 1 can be any sized container traditionally used in a pizzeria to hold dough.

The present invention device 10 includes an alarm assembly that provides a visual and/or audible alarm that indicates when a batch of dough 14 placed in the container 12 has risen to a predetermined volume. Referring to FIG. 1 in conjunction with FIG. 2, it can be seen that a lid 18 is provided for the dough container 12. The lid 18 is sized to fit over any of the dough containers 12, regardless of the size of the dough container 12. Accordingly, the lid may just fit over a large sicilian pizza dough container but may widely overlap a small regular pizza dough container.

The lid 18 has an aperture 20 formed in its center. A dough plate 22 is placed in the container on top of the batch of dough 14. The dough plate 22 includes a flat plate 24 having a bottom surface and a top surface, The bottom surface of the flat plate 24 contacts the batch of dough 14 in the container 12. The top surface of the flat plate 24 faces the lid 18. A stem shaft 26 extends upwardly from the center of the top surface of the flat plate 24.

An alarm assembly 30 is placed on top of the lid 18, over the central aperture 20. The alarm assembly 30 has a threaded neck 32 that protrudes from the bottom of the alarm assembly 30. The threaded neck 32 is sized to fit through the aperture 20 in the center of the lid 18. A clip 34 attaches to the threaded neck 32 on the alarm assembly 30. The clip 34 is larger than the central aperture 20 in the lid 18. Accordingly, when the clip 34 is attached to the threaded neck 32, the threaded neck 32 will only pass through the central aperture 20 in the lid 18 until the clip 34 contacts the lid 18. The distance D1 (FIG. 2) between the clip 34 and the base of the alarm assembly 30 can be selectively adjusted by rotating the threaded neck 32 relative the clip 34. The threads on the threaded neck 32 engage the clip 34 and cause the threaded neck 32 to move the clip 34 when the threaded neck 32 is rotated.

Depending upon the location of the clip 34, the threaded neck 32 extends through the lid 18 by a predetermined distance D2 (FIG. 1). The threaded neck 32 of the alarm assembly 30 is hollow. The interior area defined by the threaded neck 32 is large enough to receive the stem shaft 26 of the dough plate 22. Accordingly, when the dough plate 22 and alarm assembly 30 are in place, the stem shaft 26 of the dough plate 22 passes into the threaded neck 32 of the alarm assembly 30. The distance to which the stem shaft 26 enters the threaded neck 32 is determined by the position of the clip 34 on the threaded neck 32 and the height H1 of the batch of dough in the dough container 12.

Figure 2:
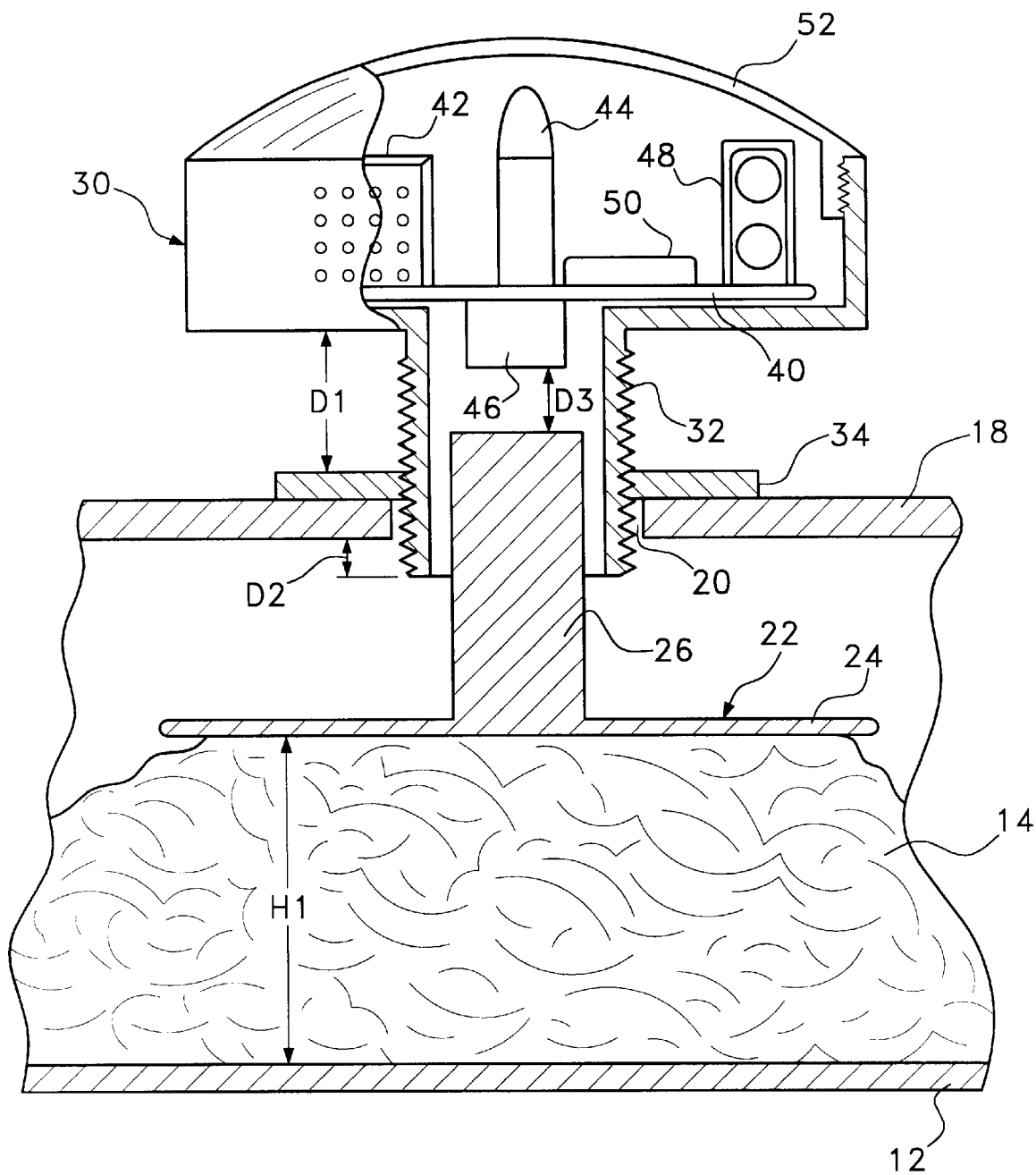
FIG. 2 is cross-sectional view of the embodiment shown in FIG. 1.

Referring solely to FIG. 2, it can be seen that within the alarm assembly 30 is positioned a circuit board 40. On the circuit board 40 are positioned an audible alarm 42, a visual alarm 44, a contact sensor 46, battery 48 and a simple control circuit 50. The contact sensor 46 is positioned at the bottom of the circuit board 40, directly above the threaded neck 32. As the batch of dough 14 in the dough container 12 rises, the stem shaft 26 of the dough plate 22 advances into the threaded neck 32 of the alarm assembly 30. The distance D3 between the contact sensor 46 and the tip of the stem shaft 26 is adjusted to correspond to the proper expansion of the rising dough 14. Accordingly, when the batch of dough 14 rises to the proper volume, the stem shaft 26 of the dough plate 22 is lifted to a point where it contacts the contact sensor 46 within the alarm assembly 30.

The contact sensor 46 causes power to be provided to the visual indicator 44 and/or the audible indicator 42. The visual indicator 44 is preferably a light, however, non-electric flag indicators may also be used. The light is visible through a transparent dome 52 on the top of the alarm assembly 30. The light is lit when the contact sensor 46 is touched by the dough plate 22. If desired, the light can be caused to periodically strobe utilizing the control circuit 50 on the circuit board. In addition to the light, the alarm assembly 30 may also contain an audible indicator 42, such as a piezoelectric buzzer. The audible indicator 42 is also triggered by the contact sensor 46. Like the light, the audible indicator 42 can be caused to periodically sound as controlled by the control circuit 50.

When the batch of dough 14 in the dough container 12 rises to the proper volume, the alarm assembly 30 sets off a visual alarm and/or an audible alarm. As such, a pizza maker will be able to tell if a particular batch of dough is ready without having to constantly monitor the dough. Additionally, since the alarm is triggered by the volume of the dough, variation in rise time, caused by temperature, humidity and ingredients are negated. A pizza maker does not have to time the dough. Rather, the pizza maker is informed when the dough is ready. Once the dough is ready, the dough is removed from the dough container and is used to make a pizza. If the dough is not needed when it is ready, it can be refrigerated until needed, thereby stopping the rising process.

It will be understood that the embodiments of the present invention system and method described and illustrated herein are merely exemplary and a person skilled in the art can make many variations to the embodiment shown without departing from the scope of the present invention. For example, the prior art is replete with different types of contact sensors, visual indicators and audible indicators. Any such prior art device can be adapted for use in the present invention. All such variations, modifications and alternate embodiments are intended to be included within the scope of the present invention as defined by the appended claims.

What is claimed is:

1. A device for determining when dough, placed within an open container, has risen to a predetermined volume, said device comprising:

a lid for covering the open container, said lid including an aperture;

an alarm assembly including a housing and a tubular neck that extends from said housing, wherein said tubular neck extends through said aperture in said lid, a mechanical adjustment mechanism that selectively engages said tubular neck above said aperture, said mechanical adjustment mechanism being too large to pass through said aperture in said lid, wherein said mechanical adjustment mechanism and said tubular neck support said housing above said lid within an adjustable range of heights;

a contact element including an enlarged, flat plate and a shaft that extends upwardly from said plate, said shaft passing into said tubular neck of said alarm assembly and activating said alarm assembly when said shaft extends into said tubular neck beyond a predetermined distance.

2. The device according to claim 1, wherein said alarm assembly contains an indicator that is activated when said shaft extends into said tubular neck beyond said predetermined distance.

3. The device according to claim 2, wherein said indicator is selected from a group consisting of visual indicators and audible indicators.

4. The device according to claim 3, wherein said visual indicators include an electrically powered light.

5. The device according to claim 3, wherein said audible indicators include an electrically powered buzzer.

6. The device according to claim 4, wherein said housing has at least one translucent section that enables said indicator to be viewed within said housing.

7. The device according to claim 1, wherein said tubular neck has a threaded exterior surface that is selectively engaged at different points by said mechanical adjustment mechanism.

8. A device for storing dough as the dough rises, said device comprising:

a container of a predetermined volume, said container having an open top through which dough can be placed into said container;

a lid for covering the container, said lid including an aperture;

a alarm assembly including a housing and a tubular neck that extends from said housing, wherein said tubular neck extends through said aperture in said lid, a mechanical adjustment mechanism that selectively engages said tubular neck above said aperture, said mechanical adjustment mechanism being too large to pass through said aperture in said lid, wherein said mechanical adjustment mechanism and said tubular neck support said housing above said lid within an adjustable range of heights;

a contact element including an enlarged plate and a shaft that extends upwardly from said plate, said shaft passing into said tubular neck of said alarm assembly and activating said alarm assembly when said shaft extends into said tubular neck beyond a predetermined distance.

9. The device according to claim 8, wherein said alarm assembly contains an indicator that is activated when said shaft extends into said tubular neck beyond said predetermined distance.

* * * * *